US 9,041,544 B2

(12) United States Patent
Bagasra (10) Patent No.: US 9,041,544 B2
(45) Date of Patent: May 26, 2015

(54) POWER OUTAGE DETECTION (75) Inventor: Abbas Bagasra, Concord, MA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 303 days.

(21) Appl. No.: 13/432,284

(22) Filed: Mar. 28, 2012

(65) Prior Publication Data

US 2013/0257623 A1    Oct. 3, 2013

(51) Int. Cl.
| | | |
|---|---|---|
| *G08B 21/00* | (2006.01) | |
| *G01R 31/00* | (2006.01) | |
| *G05D 3/12* | (2006.01) | |
| *G06F 15/173* | (2006.01) | |
| *G08B 27/00* | (2006.01) | |
| *G06F 1/30* | (2006.01) | |
| *G01D 4/00* | (2006.01) | |
| *G06F 19/00* | (2011.01) | |
| *G08B 21/02* | (2006.01) | |

(52) U.S. Cl.
CPC ............ *G08B 27/005* (2013.01); *G06F 1/30* (2013.01); *Y04S 20/36* (2013.01); *G01D 4/004* (2013.01); *G06F 19/3418* (2013.01); *G08B 21/02* (2013.01)

(58) Field of Classification Search
CPC . G06F 9/00; G06F 2009/00; G06F 2201/805; G06F 11/3051; G06F 11/0703; G06F 11/008; G06F 11/3079; G06F 1/30; G06F 8/60; G06F 9/5055; G08B 29/00; G08B 21/185; G08B 27/005; G08B 1/08; H02J 13/00; H02J 3/008; H02J 3/005; Y04S 10/30; Y04S 20/225; Y04S 10/52; Y04S 10/522; Y04S 20/36; Y04S 20/221; Y04S 40/166; Y04S 120/18; Y04S 20/22; Y04S 20/322; Y04S 20/03; H04L 2001/0092; H04L 65/00; H04L 12/2419; H04L 12/2807; H04L 12/283; H04L 2012/285; H04W 68/00; H04W 68/10; H04W 92/08; H04M 15/47; H04M 3/085; H04M 3/10; H04M 3/22; H04M 3/02; H04B 7/005; Y02B 90/246; Y02B 90/242; Y02E 60/74; G01D 4/004; H04Q 2209/60; H04J 3/22
USPC ......... 340/657, 506, 523, 541, 531, 635, 660; 700/286, 291, 293; 709/224, 223, 220; 375/135, 132; 702/59, 58, 57; 713/340, 713/320
See application file for complete search history.

(56) References Cited

U.S. PATENT DOCUMENTS

| | | | | |
|---|---|---|---|---|
| 2003/0123648 | A1* | 7/2003 | Ashton et al. | 379/403 |
| 2008/0247760 | A1* | 10/2008 | Edmon et al. | 398/128 |
| 2011/0218686 | A1* | 9/2011 | McHann et al. | 700/286 |
| 2012/0036250 | A1* | 2/2012 | Vaswani et al. | 709/224 |
| 2013/0028295 | A1* | 1/2013 | Hui et al. | 375/135 |

* cited by examiner

Primary Examiner — Mirza Alam

(57) ABSTRACT

A network device receives notification configuration information that includes a time interval criteria and a selected geographical area for providing power outage notifications. The network device receives, during a particular time interval, a loss-of-power alarm from a network interface device (NID) associated with a customer premises. The loss-of-power alarm includes a particular NID identifier. The network device retrieves, from a database, customer configuration information that associates the particular NID identifier with a particular address and identifies a power outage in a particular region associated with the particular address. The identifying is based on receiving the loss-of-power alarm and determining if other loss-of-power alarms have been received from other NIDs in the same region and within the particular time interval.

20 Claims, 9 Drawing Sheets

FIG. 5

| ONT SERIAL NUMBER | CUSTOMER ID | STREET NUMBER | STREET NAME | ZIP CODE | TIME STAMP |
|---|---|---|---|---|---|
| DFG1471056S9 | cus46uf85h | 26 | Main St. | 03038 | 14:21:2012:03:15 |
| EGF246874590 | cus56g94r7 | 57 | Main St. | 03038 | 14:21:2012:03:18 |
| YU7240497299 | cus245u88r | 124 | Elm St. | 03038 | 14:21:2012:03:15 |
| GFH240868643 | cus24958d6 | 98 | Sycamore Ln. | 03038 | 14:21:2012:03:29 |

POWER OUTAGE DETECTION

BACKGROUND

Power outage notification is a valuable feature for applications like computer-automated power distribution systems (e.g., "smart grid") and home healthcare monitoring. A power outage notification to a smart grid application can help improve operational efficiency and customer service. Current power outage notifications may rely on supervisory control and data acquisition (SCADA) systems. However, the granularity of the power outage location in such systems is limited to the transformer level, which can cover a large area. That is, when the transformer detects loss of 'load' it will trigger an alarm. Often the power outages are at a particular street or a specific address, which may go undetected at the transformer level until the customer calls to complain.

Home healthcare applications such as elderly care or chronic care rely on sensors in the home to transmit patient vitals such as blood pressure, pulse oximetry readings, etc. at a regular interval. The vitals are sent via a broadband connection through a wired and wireless modem or a gateway. If a monitoring application does not receive the vitals within a certain time interval, it creates an alarm to dispatch emergency medical help. A power outage in the home may create a false alarm due to broadband router shutdown.

DETAILED DESCRIPTION OF PREFERRED EMBODIMENTS

The following detailed description refers to the accompanying drawings. The same reference numbers in different drawings may identify the same or similar elements.

Systems and/or methods described herein may provide power outage alarm notifications to service entities, such as public utilities and/or or medical monitoring services. In one implementation, a network device may receive notification configuration information that includes a time interval criteria and a selected geographical area for providing power outage notifications to a service entity. The network device may receive, during a particular time interval, a loss-of-power alarm from a network interface device (NID) associated with a customer premises. The loss-of-power alarm may include a particular NID identifier. The network device may retrieve, from a database, customer configuration information that associates the particular NID identifier with a particular address (e.g., a customer premises address) and may identify a power outage in a particular region associated with the particular address. The network device may identify based on receiving the loss-of-power alarm and determining if other loss-of-power alarms have been received from other NIDs in the same region within the particular time interval.

Figure 1:
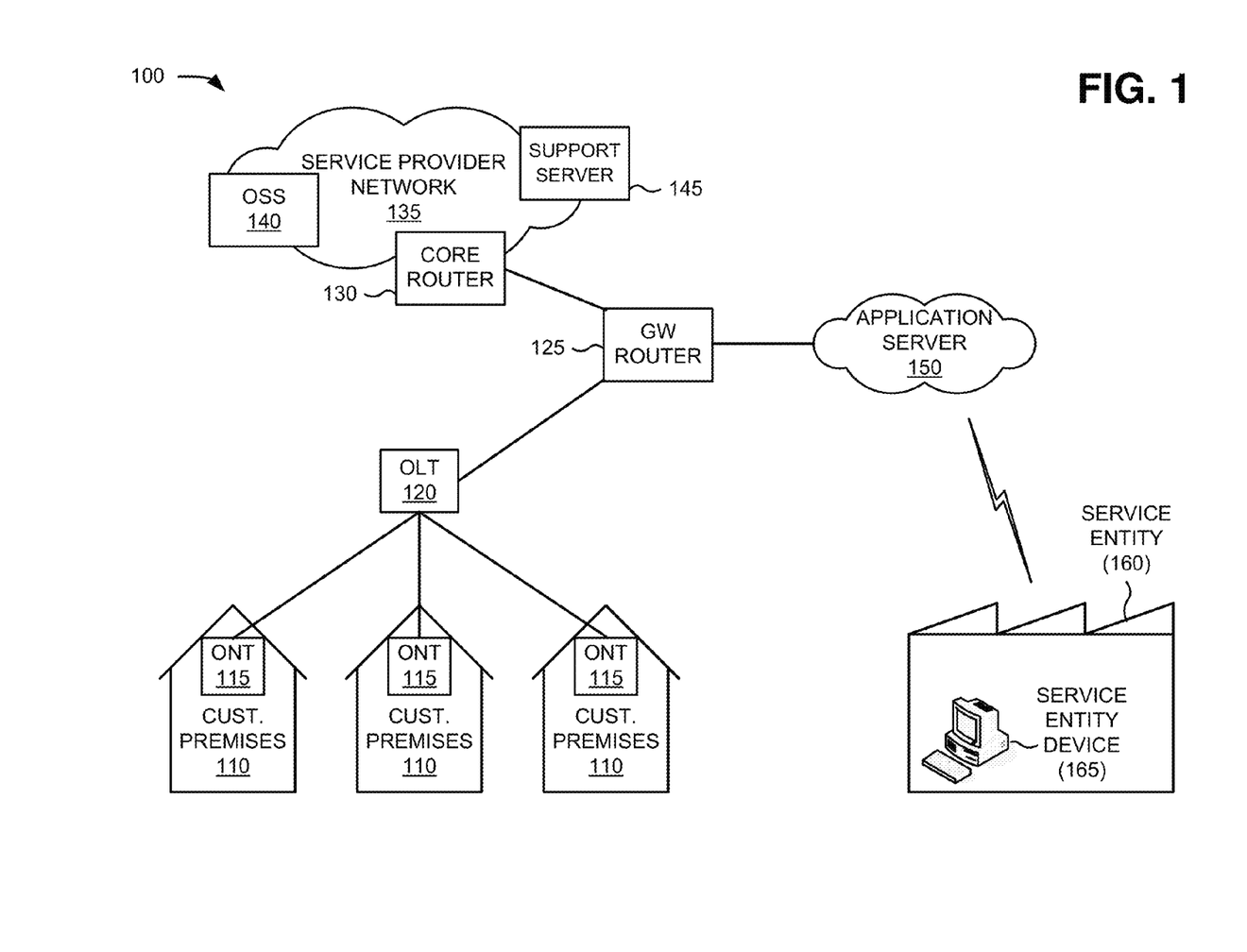
FIG. 1 is a diagram that illustrates an exemplary network environment in which systems and or methods described herein may be implemented.

FIG. 1 is a diagram that illustrates an exemplary network environment 100 in which systems and/or methods described herein may be implemented. As shown in FIG. 1, environment 100 may include customer premises 110 that each has an optical network terminal (ONT) 115, an optical line terminal (OLT) 120, a gateway router 125, a core router 130, a service provider network 135, an operations support system (OSS) 140, a customer support server 145, an application server 150, a service entity 160, and a service entity device 165. The devices and/or network of FIG. 1 may be connected via wired and/or wireless connections. The components of FIG. 1 are illustrated for simplicity. In practice, there may be more customer premises 110, ONTs, 115, OLTs 120, gateway routers 125, core routers 130, service provider networks 135, OSSs 140, customer support servers 145, application servers 150, service entities 160, or service entity devices 165. For example, there could be thousands or millions of customer premises 110.

Customer premises 110 may be connected to an electrical power grid (not shown) that may be serviced by a utility service. Customer premises 110 may include ONT 115, devices (e.g., set-top boxes, televisions, computers, etc.) and other equipment (such as routers, cables, splitters, etc., not shown) for a home network. Customer premises 110 may connect to service provider network 135 via ONT 115.

ONT 115 may include a type of network interface device (NID) that provides the termination points for a fiber line that terminates at customer premises 110. ONT 115 may provide an interface between the fiber optic line and one or more wired or wireless networks within customer premises 110. ONT 115 may thus operate to terminate an external optical network connection and present native service interfaces to subscribers/devices in customer premises 110. These services can include voice (e.g., plain old telephone service (POTS), voice over IP (VoIP) (e.g., session initiation protocol or H.248), etc.), data (e.g., Ethernet, V.35, etc.), video, and/or telemetry. In implementations described herein, ONT 115 may include a feature that recognizes an electrical power failure event. In response to the power failure, ONT 115 may automatically switch to a battery back-up mode and send a loss-of-power signal to customer support server 145. In one implementation, ONT 115 may provide repeat loss-of-power signals at regular time intervals (e.g., every minute) while ONT 115 remains in battery back-up mode.

OLT 120 may be located remotely from customer premises 110, such as, for example, at a central office associated with a service provider network 135. OLT 120 may include hardware and/or software for providing an interface between gateway router 125 and ONTs 115 or other devices (e.g., modems) located at customer premises 110. OLT unit 120 may, for instance, be responsible for allocating bandwidth to subscribers at customer premises 110 and may provide time division multiplexed (TDM) interfaces with service provider network 135.

Gateway router 125 may generally function to connect devices, such as OLT 120 and ONTs 115, to service provider network 135. Core router 130 may generally function to transmit data between other routers within service provider network 135. In addition to simply routing data, gateway router 125 and core router 130 may support other "value added" functions, such as quality of service (QoS) features, specialized security functions, such as IPsec (IP security) encryption, access control, statistics relating to multicast transmissions, or accounting features.

Service provider network 135 may include a network that distributes or makes available services, such as, for example, television services, mobile communication services, and/or Internet services. Service provider network 135 may be a satellite-based network and/or a terrestrial-based network. Service provider network 135 may include, for example, application servers, content information servers, customer information servers (e.g., OSS 140), content storage and distribution devices, billing devices, security/licensing devices, advertising information servers, etc.

OSS 140 may include servers and/or databases that provide service and inventory records of customers associated with service provider network 135. In one implementation, OSS 140 may include a database, table, or other data structure to cross-reference an ONT identifier (e.g., a unique serial number) to customer information, such as an address of customer premises 110 associated with an ONT 115.

Customer support server 145 may include one or more network devices, or other types of computational or communicative devices (e.g., a server device, an application server device, a Web server device, a database server device, a computer, etc.), to provide customer support for customers of service provider network 135. In one implementation, customer support server 145 may receive loss-of-power indications from NIDs (e.g., ONT 115 or other network termination devices) associated with service provider network 135.

Application server 150 may include one or more network devices, or other types of computational or communicative devices (e.g., a server device, an application server device, a Web server device, a database server device, a computer, etc.), to provide power outage alarm services to utility service devices 150. For example, in one implementation, application server 150 may receive an indication of an ONT 115 power outage alarm signal, query OSS 140 to match a customer premises 110 address to the alarm signal, and normalize/verify the alarm (as described further herein). Additionally, application server 150 may identify an alarm level (e.g., a category) associated with the power outage alarm signal. When particular alarm conditions are present, application server 150 may send an outage indication to service entity 160 that, for example, contracts with the service provider to receive information from service provider network 135.

Service entity 160 may include an entity (e.g., a business, organization, etc.) that may have an interest in availability of power (e.g., electrical power) to customer locations (e.g., customer premises 110 and other locations). In one implementation, service entity 160 may include a power utility entity that provides electricity to customer premises 110. In another implementation, service entity 160 may include a home health care services entity. Service entity 160 may register with service provider network 135 to receive alarm notifications for certain regions (e.g., a particular zip code, neighborhood, street, or individual address) of interest. For example, a utility company may desire more specific outage information in densely populated areas. As another example, a healthcare monitoring service may desire notification of power outages at monitored locations. Service entity 160 may include one or more service entity devices 165 to receive alarm notifications from application server 150.

Device 165 may include, for example, a communicative and/or computational device that can receive the alarm notifications. Device 165 may include, for example, a network device, a server, a personal computer, a laptop computer, a smart phone, a vehicular communication system, or other types of computational or communicational devices. In one implementation, device 165 may include a client-side application that enables device 165 to communicate with, for example, application server 150 and present information received from application server 150 to a user. In another implementation, device 165 may include an application to integrate alarm notifications from application server 150 into other information systems (e.g., outage monitoring systems).

In an exemplary operation, ONT 115 may detect a power outage at customer premises 110 and send a loss-of-power signal to support server 145. Support server 145 may associate the loss-of-power signal with a particular customer location and provide an alarm indication to application server 150. Application server 150 may filter spurious alarm data and may assign an alarm level based on, for example, criteria provided by service entity 160. Application server 150 may then provide a tiered outage indication to service entity device 165.

Although FIG. 1 shows exemplary devices of network environment 100, in other implementations, one or more devices of network environment 100 may perform one or more other tasks described as being performed by one or more other devices of environment 100.

Figure 2:
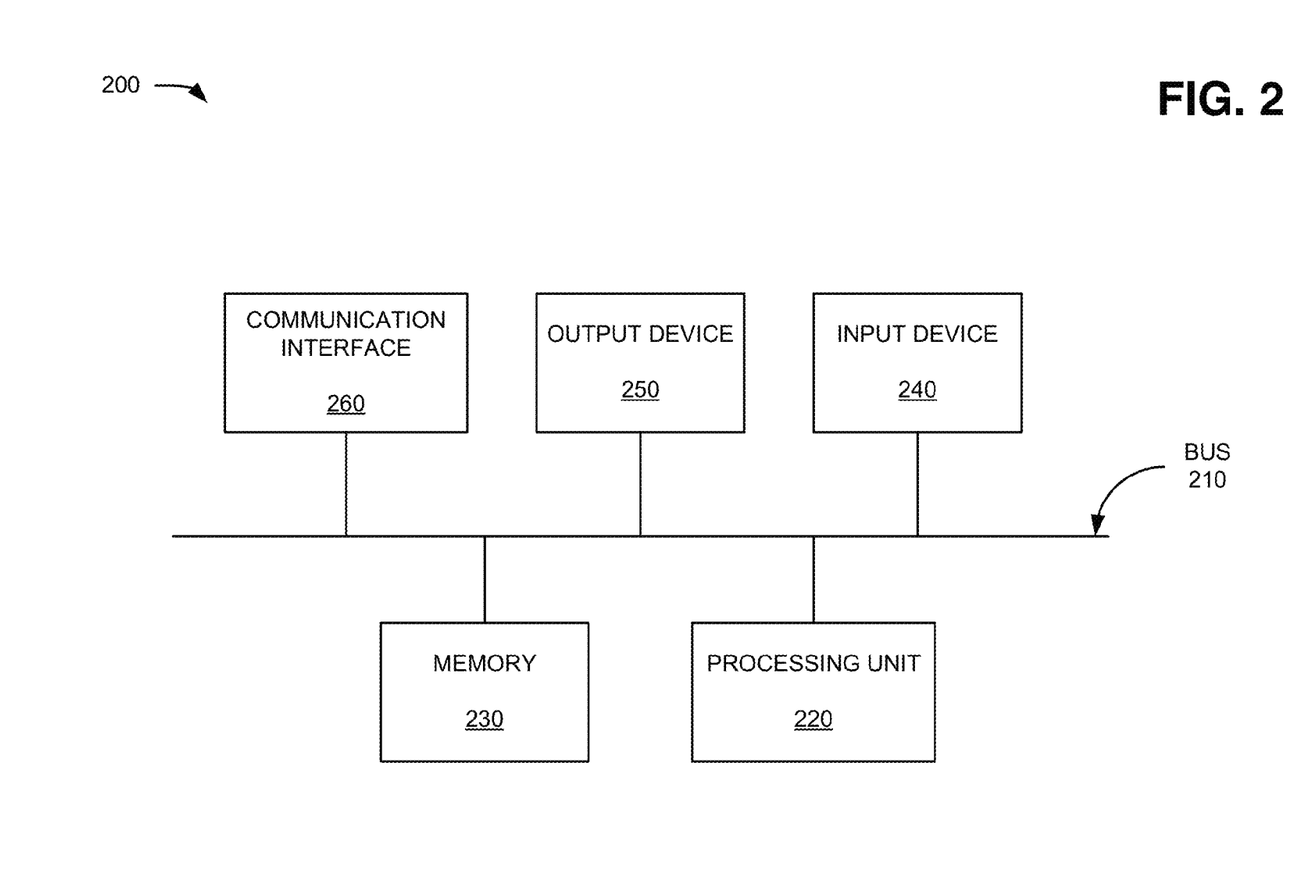
FIG. 2 is a diagram of exemplary components of a device that may be used within the network environment of FIG. 1.

FIG. 2 is a diagram of exemplary components of a device 200. Device 200 may correspond to ONT, 115, OLT 120, gateway router 125, core routers 130, OSS 140, customer support server 145, application server 150, and/or service entity device 165. Each of ONT 115, OLT 120, gateway router 125, core router 130, OSS 140, customer support server 145, application server 150, or service entity device 165 may include one or more devices 200. As shown in FIG. 2, device 200 may include a bus 210, a processing unit 220, a memory 230, an input device 240, an output device 250, and a communication interface 260.

Bus 210 may permit communication among the other components of device 200. Processing unit 220 may include one or more processors or microprocessors that interpret and execute instructions. In other implementations, processing unit 220 may be implemented as or include one or more application specific integrated circuits (ASICs), field programmable gate arrays (FPGAs), or the like.

Memory 230 may include a random access memory (RAM) or another type of dynamic storage device that stores information and instructions for execution by processing unit 220, a read only memory (ROM) or another type of static storage device that stores static information and instructions for the processing unit 220, and/or some other type of magnetic or optical recording medium and its corresponding drive for storing information and/or instructions.

Input device 240 may include a device that permits an operator to input information to device 200, such as a keyboard, a keypad, a mouse, a pen, a microphone, one or more biometric mechanisms, and the like. Output device 250 may include a device that outputs information to the operator, such as a display, a speaker, etc.

Communication interface 260 may include a transceiver (e.g., a transmitter and/or receiver) that enables device 200 to communicate with other devices and/or systems. For example, communication interface 260 may include mechanisms for communicating with other devices, such as other devices of environment 100 or another device 200.

As described herein, device 200 may perform certain operations in response to processing unit 220 executing software instructions stored by a computer-readable medium, such as memory 230. A computer-readable medium may be defined as a non-transitory memory device. A memory device may include space within a single physical memory device or spread across multiple physical memory devices. The software instructions may be read into memory 230 from another computer-readable medium or from another device via communication interface 260. The software instructions stored in memory 230 may cause processing unit 220 to perform processes described herein. Alternatively, hardwired circuitry may be used in place of or in combination with software instructions to implement processes described herein. Thus, implementations described herein are not limited to any specific combination of hardware circuitry and software.

Although FIG. 2 shows exemplary components of device 200, in other implementations, device 200 may include fewer components, different components, differently-arranged components, or additional components than depicted in FIG. 2. As an example, in some implementations, input device 240 and/or output device 250 may not be implemented by device 200. In these situations, device 200 may be a "headless" device that does not explicitly include an input or an output device. Alternatively, or additionally, one or more components of device 200 may perform one or more other tasks described as being performed by one or more other components of device 200.

Figure 3:
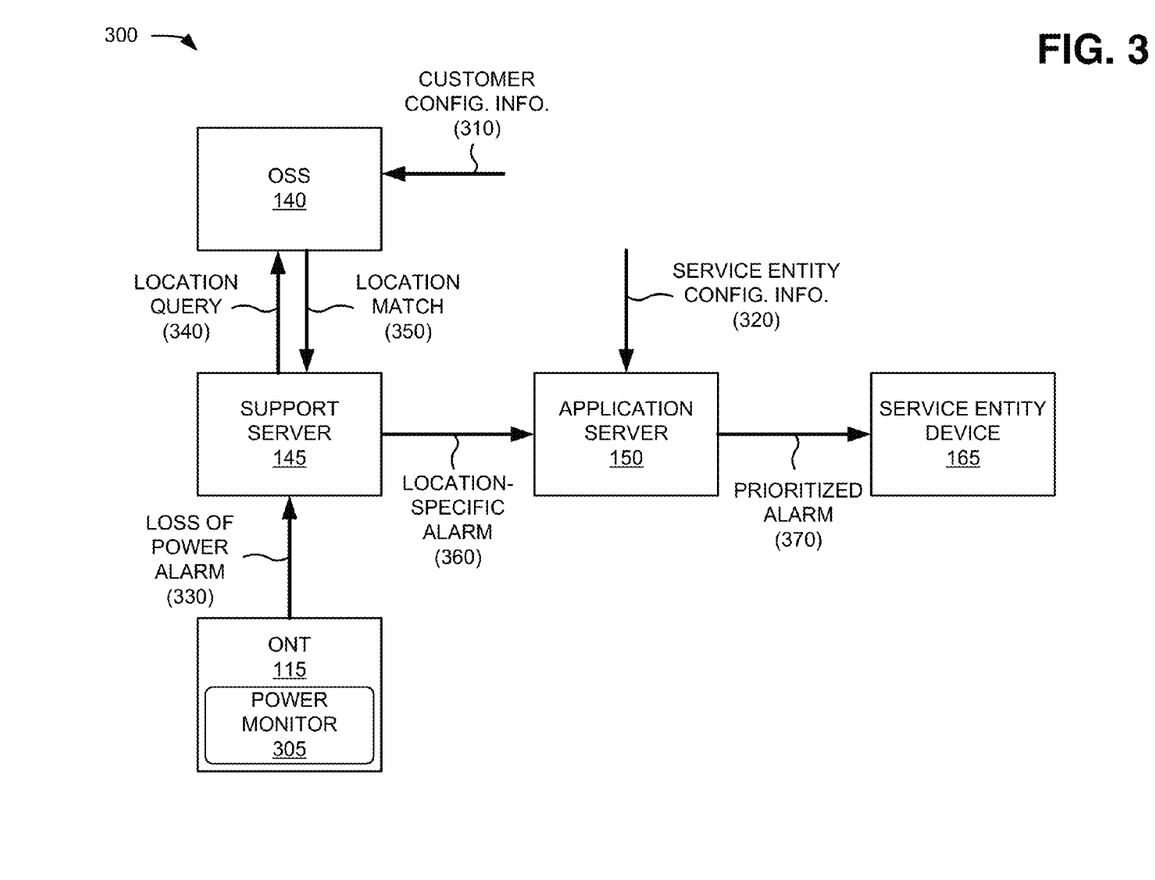
FIG. 3 is a diagram of exemplary interactions among components of a portion of the network environment of FIG. 1.

FIG. 3 is a diagram of exemplary interactions among components of a portion 300 of network environment 100. As shown in FIG. 3, network portion 300 may include ONT 115, OSS 140, support server 145, application server 150, and service entity device 165. ONT 115, OSS 140, support server 145, application server 150, and service entity device 165 may include the features described above in connection with one or more of FIGS. 1 and 2.

ONT 115 may include a power monitor application 305 that may detect a loss of electrical power coming to ONT 115. Upon detecting a loss of power to ONT 115, power monitor application 305 may be configured to switch to a battery back-up system to provide emergency power for network communications to/from ONT 115 and customer premises 110. Power monitor application 305 may also be configured to notify support server 145 when a loss of power is detected. In one implementation, ONT 115 may also include an internal clock.

OSS 140 may receive customer configuration information 310. Customer configuration information 310 may include provisioning data for customers of service provider network 135. Customer configuration information 310 may be provided, for example, from a provisioning system or another backend system (not shown) that collects information when a customer requests services from service provider network 135. In one implementation, customer configuration information 310 may include, for example, a customer name and a customer address (e.g., a physical address, including a street/building number, apartment number, street name, city name, etc., associated with customer premises 110) provided by a customer ordering services. In one implementation, customer configuration information 310 may also include a unique customer identification number (e.g., assigned by the service provider) associated with the customer name and address. Customer configuration information 310 may also include device identifiers (e.g., serial numbers of equipment, such as an ONT 115), installed at customer premises 110 to facilitate providing network services from service provider network 135. Serial numbers may include, for example, a unique alphanumeric string for each ONT 115.

Application server 150 may receive service entity configuration information 320. Service entity configuration information 320 may be provided as part of a registration process for a power outage reporting service provided by a service provider managing service provider network 135. For example, service entity configuration information 320 may include requirements of service entity 160 (e.g., a public utility, home healthcare monitoring service, etc.) such as time intervals for notifications and locations of interest. Service entity configuration information 320 may include contact information for service entity 160, such as an email address or a URL for service entity device 165. Service entity configuration information 320 may also identify regions of interest to service entity 160. For example, service entity configuration information 320 may identify a particular zip code, city, street, or street address for which service entity 160 would like to receive power outage reports. A utility company may be interested in receiving power outage reports for geographic areas where a smart grid fails to supply sufficient granularity to detect localized power outages. A home health monitoring company, by contrast, may be interested in receiving power outage reports for particular address locations (e.g., where monitored customers reside). In one implementation, service entity configuration information 320 may also include alarm level configurations for power outage reports. For example, as described further herein, service entity 160 may elect have power outage reports categorized by particular level of severity.

As shown in FIG. 3, ONT 115 (e.g., power monitor application 305) may detect a power outage and provide a loss-of-power alarm 330 to support server 145. Loss-of-power alarm 330 may include, for example, a time-stamp (e.g., indicating the time of the outage) and the serial number of ONT 115. The time-stamp may include a format of [hh:mm:YYYY:MM:DD], where "hh" is the hour (e.g., in 24-hour clock format tied to Greenwich Mean Time), where "mm" is the minute of the alarm, where "YYYY" is the calendar year, where MM is the calendar month (e.g., in numerical format), and where "DD" is the calendar day. The serial number may include a unique alpha-numeric string associated with ONT 115.

Support server 145 may receive loss-of-power alarm 330 and may query OSS 140 to retrieve the customer identity and address associated with ONT 115, as indicated by reference number 340. Location query 340 may include the serial number received from ONT 115.

In response to location query 340, OSS 140 may identify a corresponding customer identity and address associated with the serial number of ONT 115. For example, OSS 140 may compare the serial number of location query 340 against customer configuration information 310 to identify a match and then retrieve a corresponding customer identification number and address. The address may include, for example, a street number, a street name, a city name, a state abbreviation code, and a zip code. OSS 140 may provide the customer identification (ID) number and address to support server 145 as location match 350.

Support server 145 may receive location match 350 and may generate a location-specific alarm entry 360. The alarm entry may include the customer ID, the ONT serial number, the time stamp, and the customer address. In one implementation, support server 145 may provide location-specific alarm entry 360 to application server 150 for tracking in a database or another storage component.

Application server 150 may receive location-specific alarm entry 360 and may include location-specific alarm entry 360 in a database listing with other location-specific alarm entries. In one implementation, application server 150 may create a normalized alarm list. For example, application server 150 may monitor alarm entries for particular intervals (e.g., 15 minute intervals, 5 minute intervals, or another defined interval) to eliminate duplicate alarms, match fields of different alarms, and/or assign priorities to alarms (e.g., based on criteria from service entity configuration information 320, such as different priorities based on an affected coverage area). In one implementation, application server 150 may query OSS 140 to obtain additional information (e.g., a total number of ONTs 115 in a particular region) to prioritize alarms. Application server 150 may provide the prioritized alarm(s) (e.g., as prioritized alarm 370) to service entity 160 via service entity device 165.

Upon receiving prioritized alarm 370, service entity 160 may initiate an appropriate operational event. For example, a power utility may call particular customer(s) or dispatch a technician to a particular area associated with alarm 370. As another example, a healthcare monitoring service may initiate a call to a particular patient associated with a power outage location or call a respective caregiver for the particular patient.

Although FIG. 3 shows exemplary components of network portion 300, in other implementations, network portion 300 may include fewer components, different components, differently arranged components, or additional components than depicted in FIG. 3. Alternatively, or additionally, one or more components of network portion 300 may perform one or more other tasks described as being performed by one or more other components of network portion 300.

Figure 4:
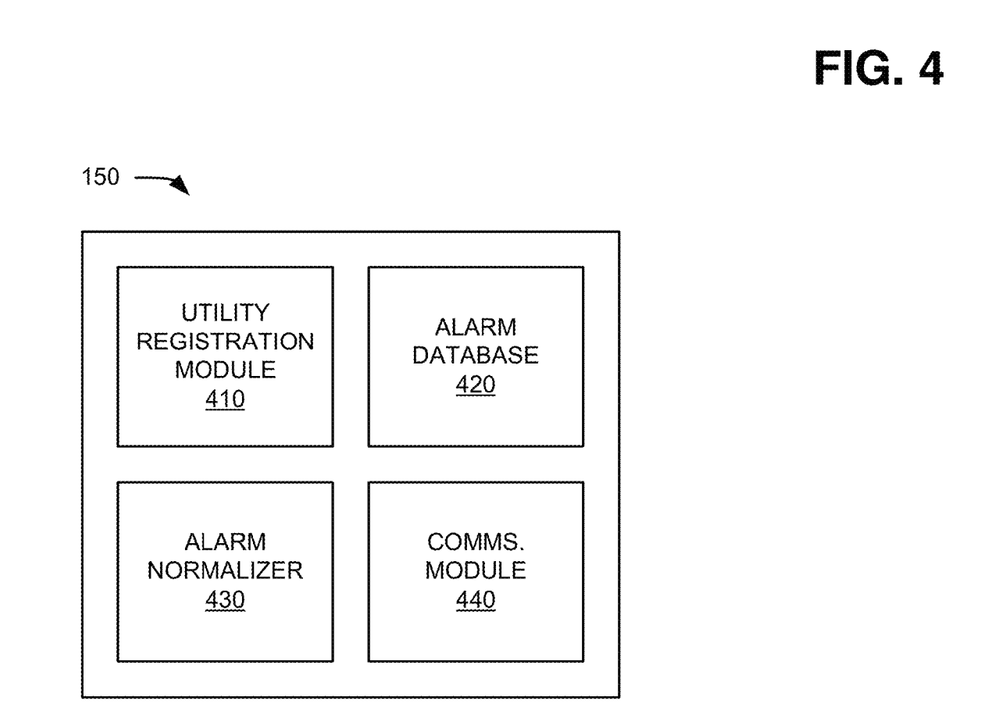
FIG. 4 is a block diagram of exemplary functional components of an application server of FIG. 1.

FIG. 4 is a block diagram of exemplary functional components of application server 150. In one implementation, the functions described in connection with FIG. 4 may be performed by one or more components of device 200 (FIG. 2). As shown in FIG. 4, application server 150 may include a utility registration module 410, an alarm database 420, an alarm normalizer 430, and a communications module 440.

Utility registration module 410 may provide an interface to solicit, receive and/or store alarm configuration information (e.g., service entity configuration information 320) for utility/care services 160. For example, utility registration module may include a web server with a user interface to solicit regions of interest to service entity 160, contact information for service entity 160, and/or alarm level configurations for power outage reports. In another implementation, service entity configuration information 320 may be collected by another system associated with service provider network 135 and provided to utility registration module 410.

Figure 5:
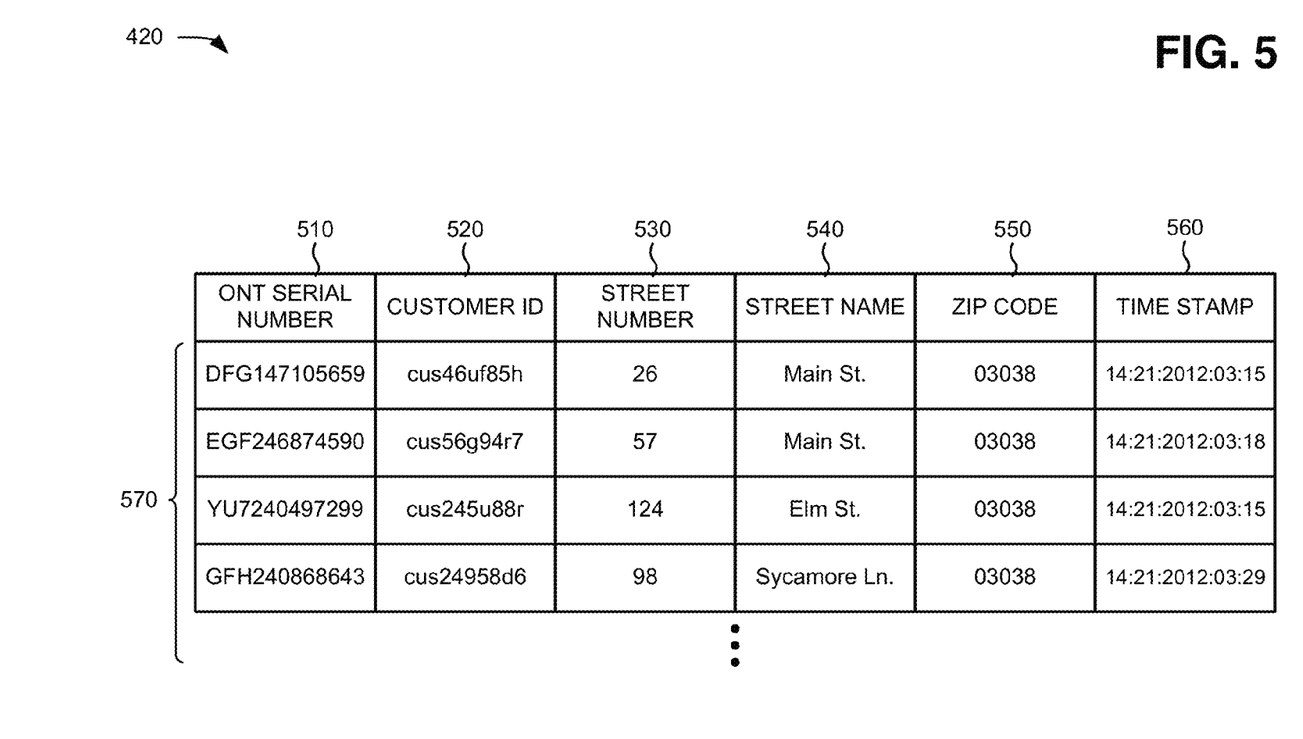
FIG. 5 is a diagram of a portion of an exemplary alarm database of FIG. 4.

Alarm database 420 may include a database, list, table, or another compilation of alarms (e.g., location-specific alarm 360) received from support server 145. Alarm database 420 is described further in connection with FIG. 5. Referring to FIG. 5, alarm database 420 may include a customer ID field 510, an ONT serial number field 520, a house number field 530, a street name field 540, a zip code field 550, and time stamp field 560, and a variety of alarm entries 570 associated with fields 510-560.

ONT serial number field 510 may include the serial numbers of ONTs 115 provided in loss-of-power alarm 330. Customer ID field 520, house number field 530, street name field 540, and zip code field 550 may include entries provided from OSS 140 (and corresponding to respective entries in ONT serial number field 510) as part of location match 350. Time stamp 560 may include time stamps for particular loss-of-power alarms 330. Each of alarm entries 570 may include data for one of fields 510-560.

According to other implementations, alarm database 420 may include additional fields, fewer fields, or different fields than shown in FIG. 5. Also, while alarm database 420 is depicted as a table, according to other implementations, alarm database 420 may take the form of some other type of data structure.

Returning to FIG. 4, alarm normalizer 430 of application server 150 may process entries from alarm database 420 over a particular time interval. The time interval may be selected (e.g., by a network administrator for service provider network 135 or service entity 160) based on the alarm application. For example, in a utility service context, the time interval may be about 15 minutes. In a home health care monitoring context, the time interval may be about 5 minutes.

Figure 6:
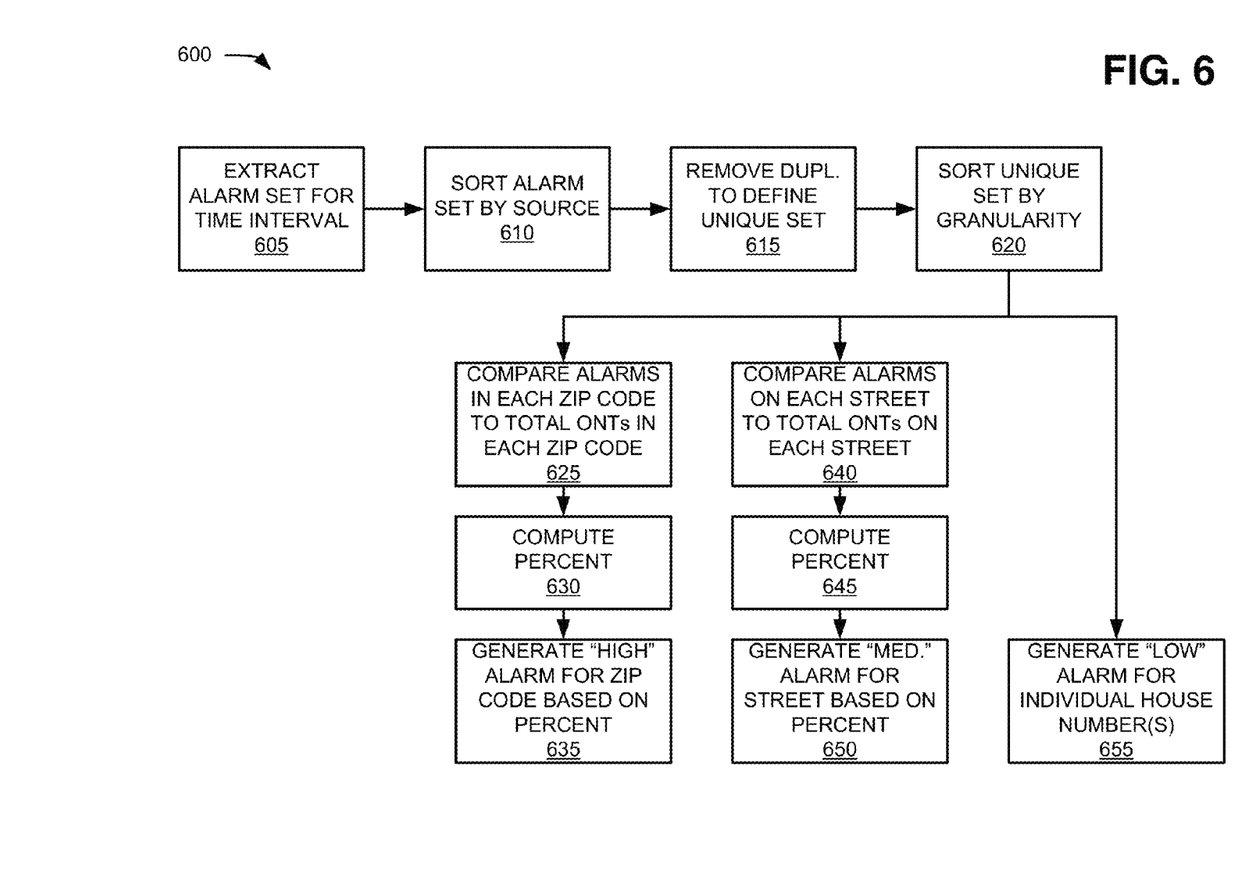
FIG. 6 is a diagram that illustrates an example of alarm processing that may be conducted by an alarm normalizer of FIG. 4.

Exemplary alarm processing 600 that may be conducted by alarm normalizer 430 is shown in FIG. 6. As shown in step 605 of FIG. 6, alarm normalizer 430 may extract an alarm set for the particular time interval. For example, alarm normalizer 430 may extract all alarms received within the previous 15 minutes (e.g., based on time-stamps of each alarm signal). In step 610, alarm normalizer 430 may sort the alarm entries (e.g., alarm entries 570) in a particular order. For example, for alarm entries 570 within the alarm set, alarm normalizer 430 may sort the alarm entries in order of customer ID field 520, then ONT serial number field 510, then house number field 530, then street name field 540, and finally zip code field 550.

In step 615, alarm normalizer 430 may eliminate duplicate alarms within the alarm set to define a unique alarm set. For example, alarm normalizer 430 may create a unique alarm list by identifying multiple alarms sent by the same ONT unit (e.g., based on ONT serial number field 510) and removing duplicate alarms with the same customer ID (e.g., from customer ID field 520) and/or ONT serial number (e.g. ONT serial number field 510). Use of both the customer ID and ONT serial number may improve accuracy and eliminate duplicate alarms from a single customer with multiple service provider accounts (e.g., a business and a residential account for the same location).

In step 620, alarm normalizer 430 may sort the unique alarm set in a particular order of granularity. For example, for alarm entries 570 within the unique alarm set, alarm normalizer 430 may sort the alarm entries in order of zip code field 550, then street name field 540, then house number field 530.

As shown in step 625, for each unique zip code, alarm normalizer 430 may compare the number of alarms in the zip code to the total number of ONTs 115 in that zip code. For example, alarm normalizer 430 may query OSS 140 to determine the number of ONTs 115 associated with a particular zip code. In step 630, alarm normalizer 430 may compute a percentage of the number of alarms (e.g., from the unique alarm set) that are in the total number of ONTs 115 in each zip code. Based on the computed percentage, in step 635, alarm normalizer 430 may send a high-priority zip code alarm report. For example, if the alarms for a particular zip code exceed 50% (or another specific value), alarm normalizer 430 may send a high-priority alarm report for the particular zip code to service entity device 165.

As shown in step 640, for each unique street name, alarm normalizer 430 may compare the number of alarms on that street to the total number of ONTs 115 on that street. For example, alarm normalizer 430 may query OSS 140 to determine the number of ONTs 115 associated with a particular street. In step 645, alarm normalizer 430 may compute a percentage of the number of alarms (e.g., from the unique alarm set) that are in the total number of ONTs 115 for each street. Based on the computed percentage, in step 650, alarm normalizer 430 may send a medium-priority street alarm report. For example, if the alarms for a particular zip code do not exceed 50% and if the alarms for a particular street (e.g., within that zip code) exceed 50% (or another specific value), alarm normalizer 430 may send a medium-priority alarm report for the particular street to service entity device 165.

As shown in step 655, if individual house numbers are not included in reports for particular zip codes or streets, alarm normalizer 430 may send a low-priority individual address report. For example, if the alarms for a particular street do not exceed 50% (or another specific value), alarm normalizer 430 may send a low-priority alarm report each individual address on a particular street to service entity device 165.

Although FIG. 6 shows exemplary steps for normalizing alarms, in other implementations, alarm normalizer 430 may apply a different process or criteria for providing alarms to service entity 160. In still other implementations, steps described as being performed by alarm normalizer 430 may be performed by another device or another functional component of application server 150.

Referring again to FIG. 4, communications module 440 of application server 150 may provide an interface to provide alarm reports to an account or device (e.g., service entity device 165) associated with service entity 160. For example, communications module 440 may receive an alarm indication from alarm normalizer 430 (e.g., a high-priority, medium priority, and/or low priority alarm) and send the alarm indication to a contact address associated with service entity 160 (e.g., in accordance with service entity configuration information 320). The alarm report may be sent, for example, as an email message, a Short Message Service (SMS) message, an instant message (IM), a mobile IM (MIM), or another message associated with an account. In other implementations, the alarm report may be provided via a URL for service entity device 165.

Although FIG. 4 shows exemplary functional components of application server 150, in other implementations, application server 150 may contain fewer, different, differently-arranged, or additional functional components than depicted in FIG. 4. In still other implementations, a functional component of application server 150 may perform one or more tasks described as being performed by another functional component of application server 150. In still other implementations, some functional components shown as being associated with application server 150 may be associated with another device (e.g., support server 145).

Figure 7:
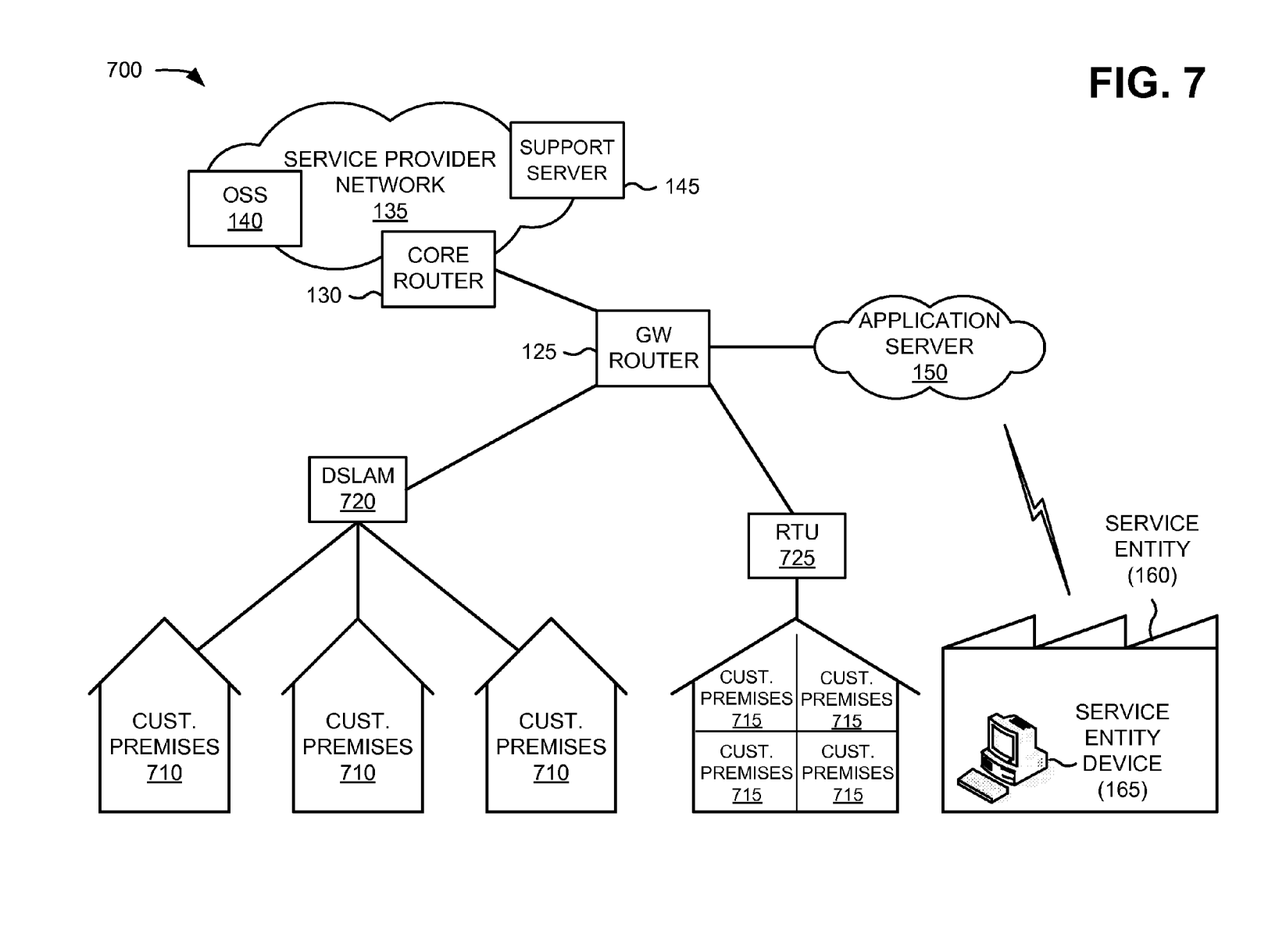
FIG. 7 is diagram that illustrates another exemplary network in which systems and or methods described herein may be implemented.

FIG. 7 is a diagram that illustrates another exemplary network environment 700 in which systems and/or methods described herein may be implemented. FIG. 7 may represent a digital subscriber line (DSL) service environment. As shown in FIG. 7, environment 100 may include customer premises 710 that are served by a digital subscriber line access multiplexer (DSLAM) 720 and other customer premises 715 that are served by a remote terminal unit (RTU) 725. Environment 100 may also include gateway router 125, core router 130, service provider network 135, OSS 140, customer support server 145, an application server 150, a service entity 160, and service entity device 165. The components of FIG. 7 are illustrated for simplicity. In practice, there may be more gateway routers 125, core routers 130, service provider networks 135, OSSs 140, customer support servers 145, application servers 150, service entity 160, service entity devices 165, customer premises 710, customer premises 715, DSLAMs 720, or RTUs 725.

Customer premises 710 and 715 may be connected to an electrical power grid (not shown) that may be serviced by a utility service. For network connectivity, customer premises 710 may connect to DSLAM 720 through a service line (e.g., copper cable) dedicated to a particular customer premises 710. Customer premises 710 may each be equipped with a DSL modem to terminate a copper loop. Customer premises 715 may connect to RTU 725 that terminates a single copper loop. Customer premises 710/715 may include, for example, one or more telephones, a home router, and one or more devices (e.g., computers, wireless devices, etc.).

DSLAM 720 may be located within a central office (e.g., remote from customer premises 710 and generally controlled by a service provider) through which customer premises 710 connect to service provider network 135. DSLAM 720 may connect multiple lines (e.g., lines from multiple customer premises 710 using DSL) to gateway router 125. Depending on its device architecture and setup, DSLAM 720 may aggregate service lines over Asynchronous Transfer Mode (ATM), frame relay, and/or an Internet Protocol network. The aggregated traffic may then be directed to gateway router 125/service provider network 135, possibly by transmitting the data through an access network (not shown). When a modem at customer premises 710 loses electrical power, DSLAM 720 may detect a loss of signal associated with the modem.

RTU 725 may terminate a single DSL line. RTU 725 may then extend the service to customer premises 715. RTU may serve a group of customers and may be located close to customer premises 715 (e.g., an apartment complex). In implementations described herein, RTU 725 may include a feature that recognizes an electrical power failure. RTU 725 may include a battery backup and may be configured to generate an alarm signal (e.g., to support server 145) when RTU 725 detects a loss of power. DSLAM 720 and RTU 725 (along with ONT 115) may be generically referred to herein as NIDs.

In an exemplary operation, DSLAM 720 may detect a loss of signal from one or more associated customer premises 710. In response to the loss of signal, DSLAM 720 may generate a loss-of-signal alarm. The loss-of-signal alarm may be provided to, for example, support server 145 or another customer support system. The loss-of-signal alarm is generally not sufficient to identify a power outage at a specific street address with reasonable accuracy. Instead, support server 145 and/or application server 150 may use the loss-of-signal alarm to detect a power outage by zip code and/or street name.

In another exemplary operation, RTU 725 may detect a loss of power. In response to the loss of power, RTU 725 may switch to a battery mode and send a loss-of-power signal to support server 145. Support server 145 may associate the loss-of-power signal with a particular location and provide an alarm indication to application server 150.

Based on loss-of-signal alarms from DSLAM 720 or loss-of-power alarms from RTU 725, application server 150 may filter spurious alarm data and may assign an alarm level based on, for example, criteria provided by service entity 160. Application server 150 may then provide a tiered outage indication to service entity device 165.

Although FIG. 7 shows exemplary devices of network environment 700, in other implementations, environment 700 may include fewer devices, different devices, differently-arranged devices, or additional devices than depicted in FIG. 7. Alternatively, or additionally, one or more devices of network environment 700 may perform one or more other tasks described as being performed by one or more other devices of environment 700.

Figure 8:
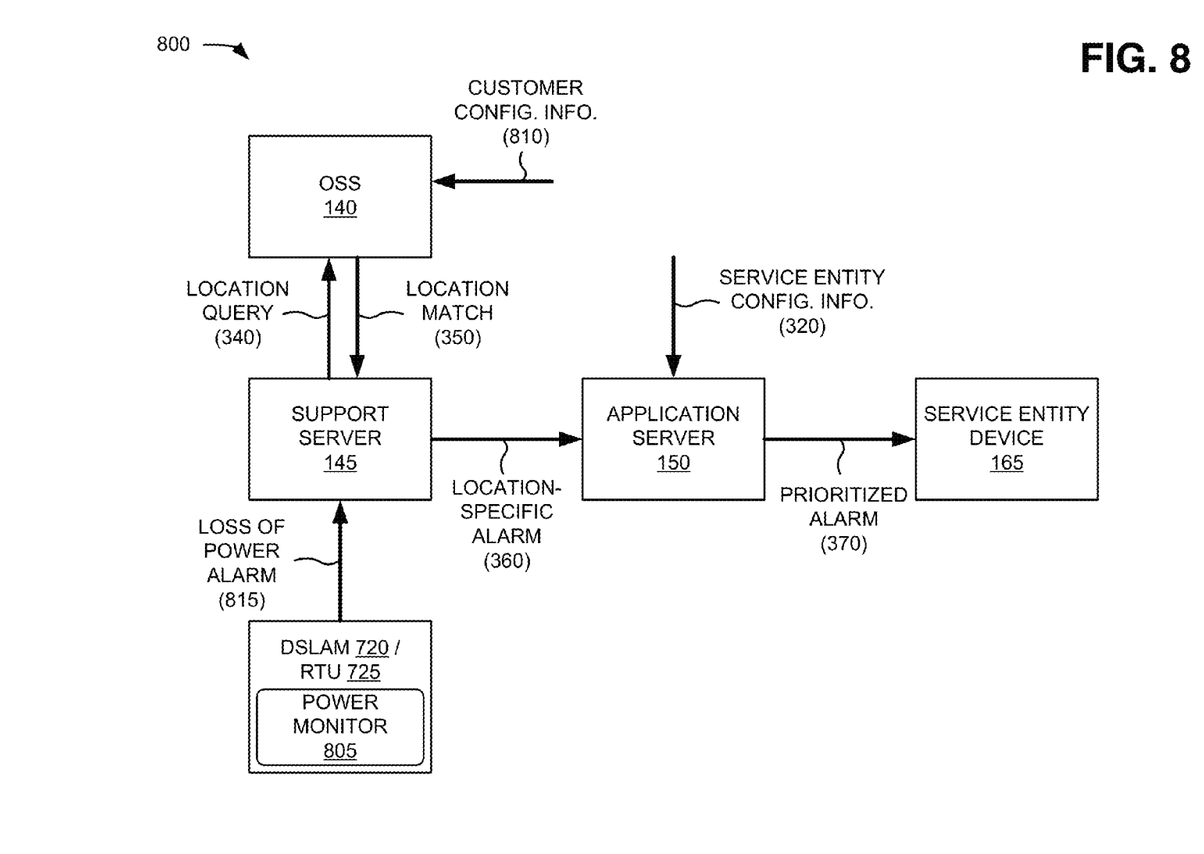
FIG. 8 is a diagram of exemplary interactions among components of a portion of the network of FIG. 7.

FIG. 8 is a diagram of exemplary interactions among components of a portion 800 of network environment 700. As shown in FIG. 8, network portion 800 may include DSLAM 720/RTU 725, OSS 140, support server 145, application server 150, and service entity device 165. DSLAM 720/RTU 725, OSS 140, support server 145, application server 150, and service entity device 165 may include the features described above in connection with one or more of FIGS. 1-7.

DSLAM 720/RTU 725 may include a power monitor application 805 that may detect a loss of electrical power coming to DSLAM 720/RTU 725 or a loss of network signal coming from a customer premises (e.g., customer premises 710/715). Upon detecting a loss of power or loss of signal, power monitor application 805 may be configured to switch to a battery back-up system (if necessary) to provide emergency power for communications between DSLAM 720/RTU 725 and other devices in environment 700. Power monitor application 805 may also be configured to notify support server 145 when a loss of power is detected. In one implementation, DSLAM 720/RTU 725 may also include an internal clock.

OSS 140 may receive customer configuration information 810. Customer configuration information 810 may include provisioning data for customers of service provider network 135. Customer configuration information 810 may be provided, for example, from a provisioning system or another backend system (not shown) that collects information when a customer requests services from service provider network 135. In one implementation, customer configuration information 810 may include, for example, a customer name and a customer address (e.g., a physical address, including a street number, apartment number, street name, city name, etc., associated with customer premises 110) provided by a customer ordering services. In one implementation, customer configuration information 810 may also include a unique customer identification number (e.g., assigned by the service provider) associated with the customer name and address. Customer configuration information 810 may also include DLS circuit identifier (CID) for DSL services provided to customer premises 710/715 associated with each customer. Depending on the DSL network arrangement the CID may be associated with one customer premises 710 or multiple customer premises 715.

As shown in FIG. 8, DSLAM 720/RTU 725 (e.g., power monitor application 805) may detect a power outage and provide a loss-of-power alarm 815 to support server 145. Loss-of-power alarm 815 may include, for example, a time-stamp (e.g., indicating the time of the outage) and the CID for DSLAM 720/RTU 725. Loss-of-power alarm 815 may be configured in a format similar to that used for loss-of-power alarm 330 (FIG. 3).

Similar to procedures described above with respect to FIG. 3, application server 150 may receive service entity configuration information 320 that determines how loss-of-power alarm 815 can be processed. Support server 145 may receive loss-of-power alarm 815 and may provide location query 340 to OSS 140 to obtain location match 350 with an address (e.g., a street number, a street name, a city name, a state abbreviation code, and a zip code) corresponding to DSLAM 720/ RTU 725. In one implementation location match 350 may include multiple addresses that may correspond to DSLAM 720/RTU 725.

Support server 145 may receive location match 350 and may generate a location-specific alarm entry 360 (e.g., to the extent of specificity enabled by location match 350). The alarm entry may include the customer ID, the ONT serial number, the time stamp, and the customer address. In one implementation, support server 145 may provide location-specific alarm entry 360 to application server 150 for tracking in a database or another storage component.

Application server 150 may receive location-specific alarm entry 360 and include location-specific alarm entry 360 in a database listing with other location-specific alarm entries. In one implementation, application server 150 may create a normalized alarm list. For example, application server 150 may monitor alarm entries for particular intervals (e.g., 15 minute intervals or another defined interval) to eliminate duplicate alarms, match fields of different alarms, and/or assign priorities to alarms (e.g., based on criteria from service entity configuration information 320). Application server 150 may provide the normalized alarm list to service entity 160 via service entity device 165.

Although FIG. 8 shows exemplary components of network portion 800, in other implementations, network portion 800 may include fewer components, different components, differently arranged components, or additional components than depicted in FIG. 8. Alternatively, or additionally, one or more components of network portion 800 may perform one or more other tasks described as being performed by one or more other components of network portion 800.

Figure 9:
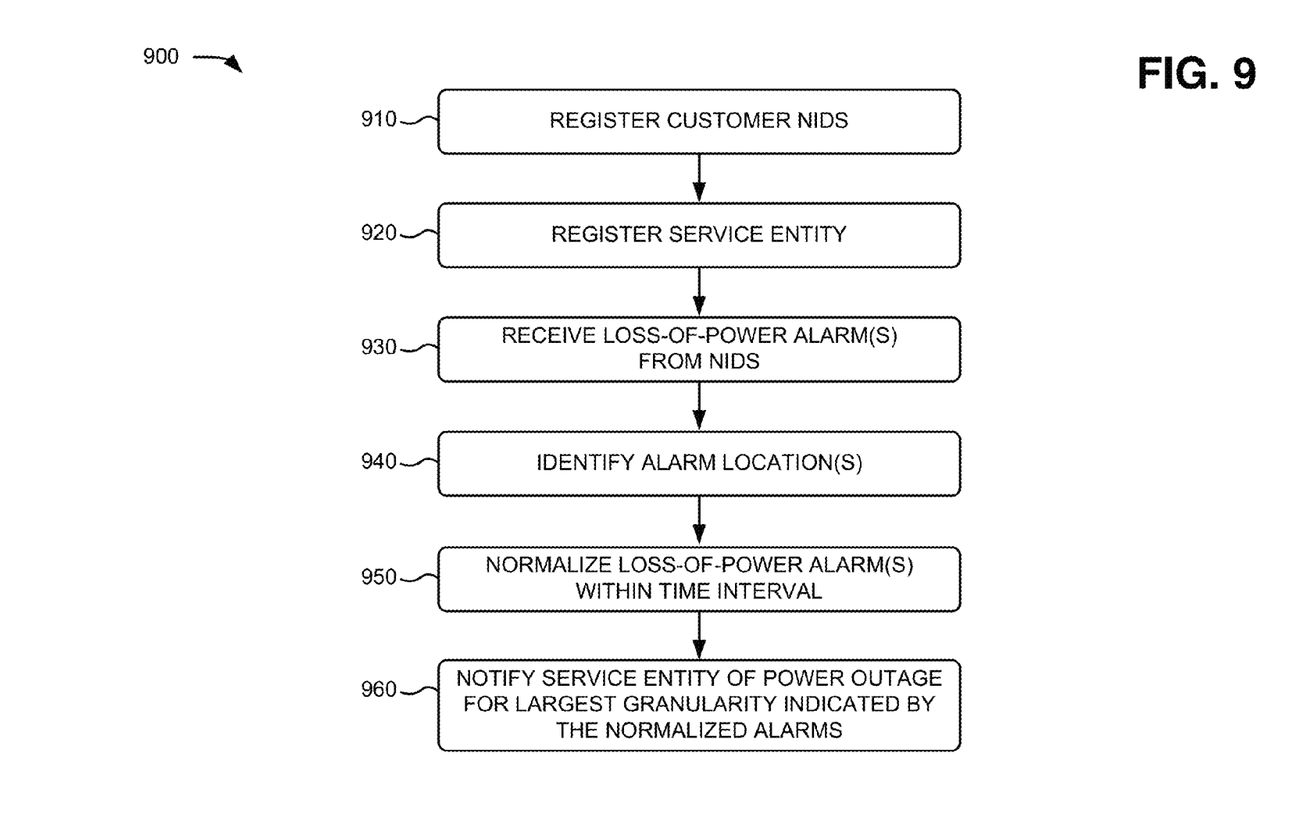
FIG. 9 is a flowchart of another exemplary process for providing a power outage notification, according to an implementation described herein.

FIG. 9 is a flowchart of an exemplary process 900 for providing a power outage notification, according to an implementation described herein. In one implementation, process 900 may be performed by support server 145. In another implementation, one or more blocks of process 900 may be performed by application server 150. In other implementations, one or more blocks of process 900 may be performed by one or more other devices or a group of devices including or excluding support server 145 and application server 150.

Process 900 may include registering one or more customer NIDs (block 910). For example, customer configuration information (e.g., customer configuration information 310/ 810) may include, for example, a customer name and a customer address (e.g., a physical address, including a street number, apartment number, street name, city name, etc., associated with customer premises 110) provided by a customer ordering services. Customer configuration information 310 may be stored, for example, in a provisioning system or another backend system that collects information when a customer requests services from service provider network 135. The customer configuration information may also include a unique customer identification number (e.g., assigned by the service provider) associated with the customer name and address. Customer configuration information further include serial numbers of equipment (e.g., ONT 115, DSLAM 720, or RTU 725) installed at or near customer premises 110 to facilitate providing network services from service provider network 135.

Process 900 may also include registering a service entity (block 920). For example, a service entity, such as a public utility or home healthcare monitoring service, may register for a power outage notification service. Application server 150 may receive service entity configuration information (e.g., service entity configuration information 320) as part of a registration process. Service entity configuration information may include requirements of service entity 160, such as time intervals for notifications, locations of interest, contact information for notifications, and/or alarm criteria.

Process 900 may further include receiving one or more loss-of-power alarms from the NIDs (block 930). For example, ONT 115 (e.g., power monitor application 305) may detect a power outage and provide a loss-of-power alarm 330 to support server 145. Loss-of-power alarm 330 may include, for example, a time-stamp (e.g., indicating the time of the outage) and the serial number for ONT 115. Similarly, DSLAM 720/RTU 725 (e.g., power monitor application 805) may detect a power outage and provide a loss-of-power alarm 815 to support server 145. Loss-of-power alarm 815 may include, for example, a time-stamp (e.g., indicating the time of the outage) and the CID for DSLAM 720/RTU 725.

Process 900 may further include identifying the alarm locations (block 940). For example, based on receiving each loss-of-power alarm, support server 145 may query OSS 140 for corresponding location information. OSS 140 may compare the serial number provided with the loss-of-power alarm against customer configuration information 310/810 to identify a match and then retrieve a corresponding customer identification number and address. The address may include, for example, a street number, a street name, a city name, a state abbreviation code, and a zip code. OSS 140 may provide the customer identification (ID) number and address to support server 145 as location match 350.

Process 900 may also include normalizing the loss-of-power alarms within a particular time interval (block 950) and notifying the service entity of a power outage for the largest granularity indicated by the normalized alarms (block 960). For example, application server 150 may receive location-specific alarm entry 360 and may add location-specific alarm entry 360 to a database listing with other location-specific alarm entries. Application server 150 may create a normalized alarm list by monitor alarm entries for a particular interval (e.g., 15 minute intervals, 5 minute intervals, or another defined interval) and eliminating duplicate alarms. Application server 150 may also apply steps described above with respect to FIG. 6, to identify multiple alarms that are indicative of a regional (e.g., zip code area, street, etc.) outage. Application server 150 may provide the normalized alarm(s) to service entity 160/service entity device 165.

Systems and/or methods described herein may receive notification configuration information that includes a selected geographical area and contact information for providing power outage notifications to a service entity. The systems and/or methods may receive, during a particular time interval, a loss-of-power alarm from a NID associated with a customer premises. The loss-of-power alarm may include a particular identifier for the NID. The systems and/or methods may retrieve customer configuration information that associates the particular identifier for the NID with a particular address. The systems and/or methods may identify a power outage in a particular region associated with the particular address based on receiving the loss-of-power alarm and determining if other loss-of-power alarms have been received from other NIDs in the particular region within the particular time interval. The systems and/or methods may send a power outage notification to the service entity using the notification configuration information.

The foregoing description provides illustration and description, but is not intended to be exhaustive or to limit the invention to the precise form disclosed. Modifications and variations are possible in light of the above teachings or may be acquired from practice of the invention. For example, while a series of blocks has been described with respect to FIG. 9, the order of the blocks may be modified in other implementations. Further, non-dependent blocks may be performed in parallel.

It will be apparent that different aspects of the description provided above may be implemented in many different forms of software, firmware, and hardware in the implementations illustrated in the figures. The actual software code or specialized control hardware used to implement these aspects is not limiting of the invention. Thus, the operation and behavior of these aspects were described without reference to the specific software code—it being understood that software and control hardware can be designed to implement these aspects based on the description herein.

Further, certain portions of the invention may be implemented as a "component" that performs one or more functions. These components may include hardware, such as a processor, an ASIC, or a FPGA, or a combination of hardware and software.

Even though particular combinations of features are recited in the claims and/or disclosed in the specification, these combinations are not intended to limit the disclosure of the invention. In fact, many of these features may be combined in ways not specifically recited in the claims and/or disclosed in the specification. Although each dependent claim listed below may directly depend on only one other claim, the disclosure of the invention includes each dependent claim in combination with every other claim in the claim set.

No element, act, or instruction used in the present application should be construed as critical or essential to the invention unless explicitly described as such. Also, as used herein, the article "a" and "one of" is intended to include one or more items. Further, the phrase "based on" is intended to mean "based, at least in part, on" unless explicitly stated otherwise.

What is claimed is:

1. A method, comprising:
   receiving, by a network device associated with a service provider network that provides television services, mobile communication services, or Internet services, notification configuration information that includes a time interval criteria and a selected geographical area of interest for providing power outage notifications;
   receiving, by the network device and during a particular time interval, a loss-of-power alarm from a network interface device (NID), for the service provider network and associated with a customer premises, wherein the loss-of-power alarm includes a particular NID identifier and indicates a loss of electrical power provided to the NID;
   retrieving, from a database in the service provider network, customer configuration information that associates the particular NID identifier with a particular address; and
   identifying a power outage in a particular region associated with the particular address, wherein the identifying is based on receiving the loss-of-power alarm and determining if other loss-of-power alarms have been received from other NIDs in the particular region within the particular time interval, and wherein the identifying comprises:
   defining an alarm set for the particular time interval;
   removing from the alarm set loss-of-power alarms from duplicate sources to form a unique alarm set;
   comparing a number of loss-of-power alarms, in the unique alarm set, that have a same zip code to a total number of NIDs for the same zip code; and
   identifying an alarm condition for the particular region to include the same zip code when the number of loss-of-power alarms is above a first threshold percentage of the total number of NIDs associated with the same zip code.

2. The method of claim 1, further comprising:
   generating a power outage notification associated with the particular region; and
   sending, based on the notification configuration information, the power outage notification to a service entity, that is different than service provider, associated with the particular region.

3. The method of claim 2, wherein the service entity associated with the particular region includes:
   a public utility, or
   a healthcare monitoring service.

4. The method of claim 1, wherein the particular region includes a particular building address.

5. The method of claim 1, wherein the identifying further comprises:
comparing a number of loss-of-power alarms, in the unique alarm set, that have a same street name to a total number of NIDs for the same street name;
identifying the alarm condition for the particular region to include the same street name when the number of loss-of-power alarms is above a second threshold percentage of the total number of NIDs associated with the same street name; and
identifying the alarm condition for the particular region to include a building number when the number of loss-of-power alarms is below the second threshold percentage of the total number of NIDs associated with the same street name.

6. The method of claim 1, wherein the time interval criteria includes a window of no more than 15 minutes.

7. The method of claim 1, wherein the NID includes:
an optical network terminal,
a remote terminal unit (RTU) for a digital subscriber line, or
a digital subscriber line access multiplexer (DSLAM).

8. A network device, comprising:
one or more memories to store a plurality of instructions; and
one or more processors configured to execute instructions in the one or more memories to:
receive notification configuration information that includes a selected geographical area and contact information for providing power outage notifications;
receive, during a particular time interval, a loss-of-power alarm from a network interface device (NID) associated with a service provider network for providing television services, mobile communication services, or Internet services to a customer premises, wherein the loss-of-power alarm includes a particular identifier for the NID and indicates a loss of electrical power provided to the NID;
retrieve customer configuration information that associates the particular identifier for the NID with a particular address;
identify a power outage in a particular region associated with the particular address, wherein the identifying is based on receiving the loss-of-power alarm and determining if other loss-of-power alarms have been received from other NIDs in the particular region within the particular time interval, wherein, when identifying the power outage in the particular region, the one or more processors are further configured to execute instructions in the one or memories to:
identify a street for the particular address,
identify a number of loss-of-power alarms, within the particular time interval, from the street,
identify a total number of NIDs associated with the street,
compare the number of loss-of-power alarms to the total number of NIDs associated with the street to determine a percentage of alarming NIDs for the street, and
define an alarm condition for the particular region to include the street when the number of loss-of-power alarms is above a threshold percentage of alarming NIDs for the street; and
send, based on the notification configuration information, a power outage notification to a service entity.

9. The device of claim 8, wherein the particular region includes one of:
a geographic area associated with a zip code,
a particular street, or
a particular building address.

10. The device of claim 8, wherein, when identifying the power outage in the particular region, the one or more processors are further configured to execute instructions in the one or more memories to:
identify a zip code for the particular address;
identify a number of loss-of-power alarms, within the particular time interval, from the zip code;
identify a total number of NIDs within the zip code;
compare the number of loss-of-power alarms to the total number of NIDs within the zip code to determine a percentage of alarming NIDs within the zip code; and
define an alarm condition for the particular region to include the zip code when the number of loss-of-power alarms is above a threshold percentage of alarming NIDs for the zip code.

11. The device of claim 8, wherein the NID includes:
an optical network terminal,
a remote terminal unit (RTU) for a digital subscriber line, or
a digital subscriber line access multiplexer (DSLAM).

12. A method, comprising:
receiving notification configuration information that includes a time interval criteria and a selected geographical area of interest for providing power outage notifications;
receiving, during a particular time interval, a loss-of-power alarm from a network interface device (NID) associated with a customer premises, wherein the loss-of-power alarm includes a particular NID identifier;
retrieving, from a database, customer configuration information that associates the particular NID identifier with a particular address; and
identifying a power outage in a particular region associated with the particular address, wherein the identifying is based on receiving the loss-of-power alarm and determining if other loss-of-power alarms have been received from other NIDs in the particular region within the particular time interval, and wherein the identifying comprises:
defining an alarm set for the particular time interval;
removing from the alarm set loss-of-power alarms from duplicate sources to form a unique alarm set;
comparing a number of loss-of-power alarms, in the unique alarm set, that have a same street name to a total number of NIDs for the same street name; and
identifying an alarm condition for the particular region to include the same street name when the number of loss-of-power alarms is above a threshold percentage of the total number of NIDs associated with the same street name.

13. The method of claim 12, wherein the identifying further comprises:
comparing a number of loss-of-power alarms, in the unique alarm set, that have a same zip code to a total number of NIDs for the same zip code; and
identifying an alarm condition for the particular region to include the same zip code when the number of loss-of-power alarms is above a different threshold percentage of the total number of NIDs associated with the same zip code.

14. The method of claim 12, wherein the identifying further comprises:
identifying an alarm condition for the particular region to include a building number when the number of loss-ofpower alarms is below the threshold percentage of the total number of NIDs associated with the same street name.

15. The method of claim 12, further comprising:
generating a power outage notification associated with the particular region; and
sending, based on the notification configuration information, the power outage notification to a service entity, that is different than service provider, associated with the particular region.

16. The method of claim 15, wherein the power outage notification includes one or more of:
a Short Message Service (SMS) message,
an instant message (IM),
a mobile IM (MIM), or
an email message.

17. The method of claim 15, wherein the service entity associated with the particular region includes:
a public utility, or
a healthcare monitoring service.

18. The method of claim 12, wherein the time interval criteria includes a window of no more than 15 minutes.

19. The method of claim 12, wherein the NID includes a battery back-up system.

20. The method of claim 12, further comprising:
monitoring, for the particular time interval, for additional loss-of-power alarms from the NID; and
determine to send a power-outage alarm when an additional loss-of-power alarm is received from the NID within the particular time interval.

* * * * *